United States Patent
Michelsson

(10) Patent No.: US 8,264,534 B2
(45) Date of Patent: Sep. 11, 2012

(54) METHOD AND APPARATUS FOR PROCESSING THE IMAGE DATA OF THE SURFACE OF A WAFER RECORDED BY AT LEAST ONE CAMERA

(75) Inventor: Detlef Michelsson, Wetzlar-Naunheim (DE)

(73) Assignee: Vistec Semiconductor Systems GmbH, Weilburg (DE)

( * ) Notice: Subject to any disclaimer, the term of this patent is extended or adjusted under 35 U.S.C. 154(b) by 940 days.

(21) Appl. No.: 12/315,589

(22) Filed: Dec. 4, 2008

(65) Prior Publication Data

US 2009/0153657 A1 Jun. 18, 2009

(30) Foreign Application Priority Data

Dec. 12, 2007 (DE) .................. 10 2007 060 355

(51) Int. Cl.
 *H04N 7/18* (2006.01)
(52) U.S. Cl. ........ 348/126; 382/144; 382/145; 382/146; 382/147; 382/148; 382/149; 382/150; 382/151; 382/152
(58) Field of Classification Search .......... 382/144–151; 348/126
See application file for complete search history.

(56) References Cited

U.S. PATENT DOCUMENTS

| | | | | |
|---|---|---|---|---|
| 5,768,443 A * | 6/1998 | Michael et al. | ................. | 382/294 |
| 5,982,452 A * | 11/1999 | Gregson et al. | ................. | 348/584 |
| 6,407,809 B1 * | 6/2002 | Finarov et al. | ............. | 356/237.3 |
| 6,512,843 B1 | 1/2003 | Kuwabara | ..................... | 382/149 |
| 6,941,009 B2 * | 9/2005 | Wienecke | ..................... | 382/149 |
| 7,075,565 B1 * | 7/2006 | Raymond et al. | ............. | 348/126 |
| 7,184,612 B2 | 2/2007 | Naftali et al. | ................. | 382/304 |
| 7,215,808 B2 | 5/2007 | Miller | ............................ | 382/145 |
| 7,221,992 B2 | 5/2007 | Smith et al. | .................... | 700/110 |
| 7,512,260 B2 * | 3/2009 | Murakami et al. | ............. | 382/145 |
| 2002/0109112 A1 * | 8/2002 | Guha et al. | ............... | 250/559.46 |
| 2004/0165764 A1 | 8/2004 | Michelsson | .................... | 382/147 |
| 2005/0008217 A1 | 1/2005 | Luu et al. | ....................... | 382/145 |
| 2005/0031189 A1 * | 2/2005 | Richter | ......................... | 382/145 |
| 2006/0204109 A1 | 9/2006 | Michelsson et al. | .......... | 382/219 |
| 2006/0279729 A1 * | 12/2006 | Heiden et al. | .............. | 356/237.5 |
| 2007/0064224 A1 | 3/2007 | Kreh et al. | ................... | 356/237.2 |
| 2008/0260296 A1 * | 10/2008 | Chung et al. | .................. | 382/307 |

FOREIGN PATENT DOCUMENTS

| | | |
|---|---|---|
| DE | 103 07 373 | 9/2004 |
| DE | 103 07 373 A1 | 9/2004 |
| DE | 103 31 593 | 2/2005 |
| DE | 103 43 148 | 4/2005 |
| DE | 10 2005 011 237 B3 | 8/2006 |
| DE | 10 2005 027 120 | 12/2006 |

* cited by examiner

*Primary Examiner* — Duyen Doan
(74) *Attorney, Agent, or Firm* — Davidson, Davidson & Kappel, LLC

(57) ABSTRACT

A method for processing the image data of the surface of a wafer (2) recorded by at least one camera (5) is disclosed, wherein an image field (15) is defined for each camera (5) in such a way that the recorded image content is repeated after N recorded images. In an evaluation electronics (18) M utility programs (19) are determined, wherein M is equal to the number of recorded images after which the image content is repeated. The number M of utility programs (19) is adapted to the number N of images. Each of the M utility programs (19) of the plurality of recorded images is only fed with images having the same image contents in order to detect defects on the basis of the image contents of the images of the surface of the wafer. The results of the M utility programs (19) are respectively forwarded to a central program (20) in a sequential manner, which compiles a distribution of the defects present on the surface of the wafer (2) from the individual results of the M utility programs (19).

19 Claims, 8 Drawing Sheets

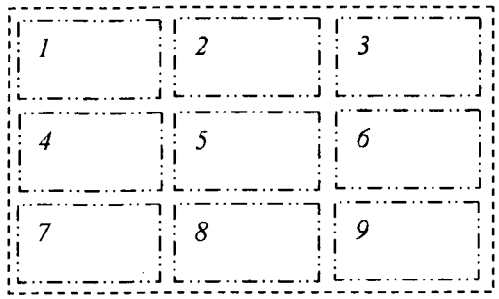
Fig. 5a
Fig. 5b
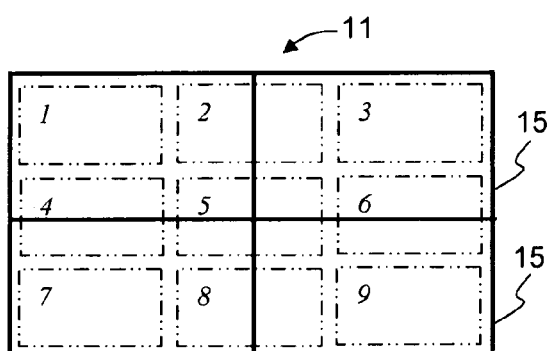
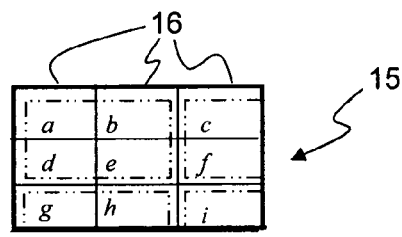
Fig. 5c
Fig. 5d
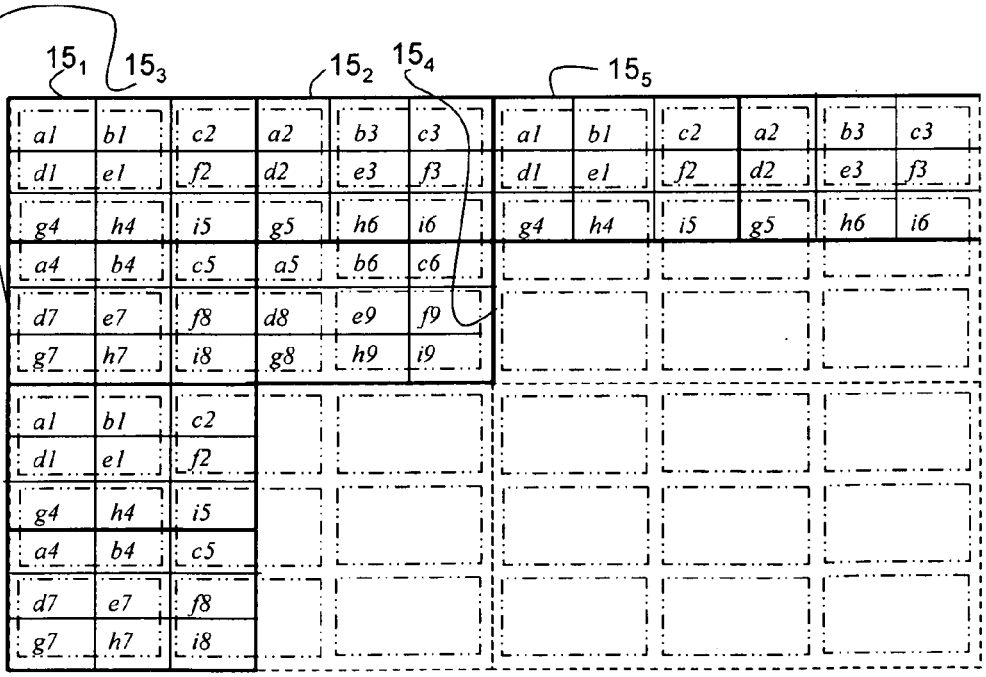
Fig. 5e

METHOD AND APPARATUS FOR PROCESSING THE IMAGE DATA OF THE SURFACE OF A WAFER RECORDED BY AT LEAST ONE CAMERA

This claims the benefits of German Patent Application No. 10 2007 060 355.1, filed on Dec. 12, 2007, and hereby incorporated by reference herein.

The present invention relates to a method for processing the image data of the surface of a wafer recorded by at least one camera. In particular, the present invention relates to a method for processing the image data of the surface of a wafer recorded by at least one camera, wherein a relative movement is carried out between the wafer and the at least one camera.

Further, the present invention relates to an apparatus for processing the image data of the surface of a wafer recorded by at least one camera. In particular, the present invention relates to an apparatus for processing the image data of the surface of a wafer recorded by at least one camera, wherein the apparatus comprises a means for creating a relative movement between the wafer and the at least one camera, and wherein an image field (camera field) is formed for each camera.

A structured semiconductor consists of dies and the streets between the dies. A certain number of dies are exposed by means of a stepper in one go. The area on the wafer exposed in one shot or exposure is referred to as stepper area window (SAW). Since all SAWs on a semiconductor wafer are exposed with the same mask, all structures of the dies are at the same position in each SAW.

BACKGROUND

From U.S. Pat. No. 6,512,843, a method is known wherein adjacent dies are compared to one another. Herein, the exposures and the dies each have the same size so that they are comparable. Only the edge areas are compared at irregular intervals. In this approach, however, the full camera exposure capabilities are usually not considered. The camera often records much more than is actually necessary for subsequent comparison. This leads to an unnecessary increase in data, which in turn leads to the system being slowed down.

U.S. Pat. No. 7,184,612 discloses a method and an apparatus for parallel processing of data in a wafer inspection system, wherein no communication or synchronization is needed between the individual process nodes. The approach is based on hardware, wherein the detection area is subdivided into a fixed number of blocks due to the fact that the number of groups of process nodes is also fixed due to fixed wiring.

From U.S. Pat. No. 7,215,808, an image processing system for error detection is known. The system comprises a plurality of processors for recording image data from a substrate. The analysis of one or more selected portions of such an image can also be carried out to see whether the substrate has a defect. The system comprises a plurality of buses to connect the individual processors to each other, wherein the data transfer speed per bus is 50 gigabits per second or more, and the error rate is below about $10^{-16}$. Again, this is a hardware realization with a fixed number of buses, processors and lines.

From U.S. Pat. No. 7,221,992, a method and an apparatus are known for parallel data processing for error detection in a wafer inspection system. A data distribution system comprises a plurality of data distribution nodes, which are interconnected via a plurality of data transmission paths. This configuration enables data collected by any desired type of detector to be forwarded to respective ones of the plurality of process nodes. This, in turn, enables the implementation of a plurality of possible algorithms for error analysis.

German patent application DE 103 07 373 A1 discloses a method and an apparatus for optical analysis of wafers, the structures of which have been created by SAWs. The invention takes into account that depending on the stepper and the size of the dies (design), the size of the SAW varies substantially. Generally, it cannot be expected that an SAW can be imaged with one camera image. This is why an SAW is preferably subdivided into regular, equally sized logical portions (SAW segments). Each logical SAW segment has a SAW segment index associated with it. An image field of the camera can only cover a certain number of these SAW segments. Each segment of an image field, also referred to as an image field segment, has an index associated with it, also referred to as an image field segment index.

German patent application DE 103 31 593 A1 discloses a method for defect segmenting in structures on semiconductor substrates. After recording an image of a semiconductor substrate, identical structures or structural elements are subtracted from one another. The resulting difference function is compared with a top and bottom threshold for the detection of defects.

German patent application DE 103 43 148 A1 discloses a method and an apparatus for inspecting a wafer, wherein at least one segment of a surface of a wafer is illuminated, an image of the illuminated segment is detected by an image detection means, at least one image area in the detected image is determined, and a size of the image area of the image detection means is changed on the basis of the at least one image area. For determining the image area, a pattern detection software looks for characteristic structures in the detected image. By changing the image field size, optionally either the throughput or the resolution of the wafer inspection apparatus can be optimized, and the image field can always be optimally adapted to the shot size of the wafer.

German patent application DE 10 2005 027 120 A1 discloses a method for inspecting a wafer, wherein the wafer has a first area of periodically arranged SAWs and at least one second area of SAWs displaced with respect to the first area. The method shows the process steps of optically recording the first area of the wafer by moving an imaging window in the period direction, displacing the imaging window relative to the wafer, optically recording the second area of the wafer by moving the displaced imaging window in the period direction, and evaluating the image by comparing partial images.

SUMMARY OF THE INVENTION

The amount of data created during wafer inspection by recording images of the wafer areas to be inspected and the analysis of potential defects, rises substantially as the resolution of the images increases. At a resolution of 30 μm and the use of a camera with a 3CCD chip, the amount of data per wafer is about 280 MBytes. If the resolution is increased to 10 μm, the amount of data is increased nine-fold. Even with the increased computing power of today's processors, analyzing and processing such large amounts of data is not easy, let alone quick.

To solve these problems, it is state of the art, as described above, to distribute the data to different processes and therefore to a plurality of fixedly wired processors or a plurality of computers (cluster). Herein, usually, a single data processing module (DP module, utility program) is used for all data, and the data channels are distributed to different DP modules. The data are usually regularly distributed to the various DP modules. The use of only one DP module only incompletely utilizes the hardware, however, and it is not possible to scale computing power. If the data are distributed according to color channels, there is a high demand for communication between the DP modules. The even distribution of the data without regard to the data contents, also requires communication between the DP modules.

The communication between the DP modules is also necessary to achieve good scalability of system output.

It is an object of the present invention to provide a method adapted to the conditions of different wafer structures or architectures, so that the images of the surface of a wafer recorded by at least one camera are efficiently processed, the existing hardware is efficiently used, and different image contents are taken into consideration.

The present invention provides a method for processing image data of the surface of a wafer recorded by at least one camera, wherein a relative movement is carried out between the wafer and the at least one camera, comprising the steps of:
- defining an image field for each of said cameras in such a way that the recorded image content of said image field is repeated after N recorded images, wherein N is equal to or greater than two;
- determining M utility programs in an evaluation electronics, wherein M is equal to the number of recorded images after which the image content of the image fields is repeated, and adapting the number M of utility programs to the number of N images;
- feeding only images having the same image content of the image fields from the plurality of recorded images to each of the M utility programs to detect defects based on the image content of the image fields of the images from the surface of the wafer; and
- sequentially feeding the respective results of said M utility programs to a central program, which compiles a distribution of the defects present on the surface of the wafer from the individual results of said M utility programs.

It is an alternate or additional an object of the present invention to provide an apparatus adapted to the conditions of different wafer structures or architectures, so that the images of the surface of a wafer recorded by at least one camera are efficiently processed, the existing hardware is efficiently used, and different image contents are taken into consideration.

The present invention provides an apparatus for processing the image data of the surface of a wafer recorded by at least one camera, comprising: a means for creating a relative movement between the wafer and the at least one camera; an image field is assigned to each camera, wherein said image field of each camera is adaptable in such a way that the recorded image content of said image field is repeated after N recorded images, wherein N is equal to or greater than two; an evaluation electronics with M utility programs, wherein M is equal to the number of recorded images after which the image content of the image fields is repeated, and in that the number M of utility programs is adapted to the number N of images, in that each of the M utility programs only receives images from the plurality of recorded images having the same image content of the image fields, in order to detect defects on the basis of the image content of the image fields of the images of the surface of the wafer; and a central program which sequentially receives the individual results of the M utility programs and compiles a distribution of the defects present on the surface of the wafer from the individual results of the M utility programs.

As an introduction to the description of the present invention, it should be noted that, for an abstract description, the SAW will be considered as a single, repetitive structure in the following. The method is also applicable to other repetitive structures.

In the method according to the present invention, the image data of the surface of a wafer recorded by at least one camera may be processed. The at least one camera is traversed across the wafer in a relative movement and records a plurality of images. Each image contains a certain segment of the wafer. An image field is defined for each camera in such a way that the recorded image content is repeated after N recorded images, wherein N is equal to or greater than two.

In particular, structures on the wafer may be inspected which have been created with the aid of the stepper area window. In one embodiment of the present invention, the image fields of the cameras are adapted to the structures on the wafer in such a way that after a predefined number N of recorded images, the image content of the image field is repeated. For this purpose, the cameras must be adjusted accordingly.

In one preferred embodiment of the method, it is taken into account that depending on the stepper and the die size (design) the size of the SAW varies substantially. Generally, it can be expected, however, that an SAW can be imaged with a camera image. This is why the size of the image field of the at least one camera is determined in such a way that each SAW is divided into regular, even sized logical SAW segments in an initializing step. Also, each logical SAW segment has an SAW segment index associated with it. The choice of the division of the SAW into SAW segments, is therefore carried out such that an image field contains a whole number of SAW segments.

Additionally, in the preferred embodiment, the image field of the camera is divided into SAW-segment-imaging image field segments in such a way that after a predetermined interval of recorded image fields, there is a repetition of an identical association of imaged SAW segments in image field segments, wherein image field segments are smaller, larger or displaced with respect to the SAWs, so that the repetition interval is greater than one (N>=2):

An image field of the at least one camera can only include a certain number of these SAW segments. For determining which image field segments include which SAW segments, in another embodiment, each image field segment is associated with an index, referred to as image field segment index in the following. Thus both the logical SAW segments and the image field segments are indexed. The image fields have a combination of the SAW segment index and the image field segment index associated with them, based on which a determination of the image field segments to be compared is made. When the SAW segment division is carried out properly, groups of images result in which exactly one SAW segment index is associated with each image field segment index. Within such a group, all image fields have the same content, and correspondingly, only those image field segments are compared with each other which have an identical combination of the SAW segment index and the image field segment index. This division into N image groups can be carried out in a training phase.

The division into N image groups can be carried out, for example, according to the method disclosed in the above-mentioned German patent application DE 103 07 373 A1, wherein the above-described independence of data exists. The method according to the present invention, however, is not limited to this method according to the prior art, but is generally applicable in all cases where the division into groups results in images independent to such a degree that the M utility programs can also be executed independently from each other.

M utility programs (DP modules) may be determined in an evaluating electronics, wherein M is equal to the number N of groups having an identical association of the image field segment index and the SAW segment index. If images of the wafer are recorded, each image is associated with exactly one utility program. The data for each of the N groups in each case is independent of all data of the other groups. This independence is utilized by the method according to the present invention in the division into groups of images, image fields, SAWs and SAW segments: only that number of independently running utility programs is used which is actually necessary for the analysis of the images. The independence of the data is a necessary precondition for the method according to the present invention, because the communication between the M utility programs can be omitted, which results in a substantial increase in efficiency.

From the plurality of recorded images only images with the same image contents may be provided to each of the M utility programs to detect defects on the basis of the image contents of the images of the surface of the wafer. In one embodiment, each of the at least one cameras is connected to one frame grabber, respectively. The outputs of the frame grabbers are coupled to a control means. The recorded images are first forwarded by the cameras to the frame grabber respectively associated with a particular camera. Subsequently, the control means determines the associated utility program and returns the response to the respective frame grabber. Finally, the images are distributed by the frame grabbers according to the respective image contents to the appropriate one of the M utility programs.

The respective results of the M utility programs may be sequentially forwarded to a central program which compiles a distribution of the defects present on the surface of the wafer and supplies an overall result from the individual results of the M utility programs.

Optionally, further preferred embodiments are possible for the method according to the present invention, as described in the following.

As the at least one camera, a line camera and/or an array camera is usable, which is capable of making microscopic and/or macroscopic images. If only one line is used for imaging, the logical SAW segments must be subdivided according to the width of one pixel. All other algorithms for the division into comparable segments remain unchanged. The wafer can be illuminated with a constant light source when a line camera is used.

Usually, the wafer is, preferably continuously, moved below the camera. It is also conceivable, however, for the camera to be moved relative to the wafer. The individual images of the at least one camera are achieved by opening a shutter and triggering a corresponding flash. The triggering of the flash is carried out as a function of the relative position of the wafer, which is indicated by corresponding position parameters of the measuring stage moving the wafer.

As described above, the size of the SAWs can vary depending on the type of wafer. It is therefore suitable for the size of the SAWs to be transmitted to the routine determining the number N of images, and the corresponding dies to be marked, so that based on knowledge about the size of the image field of the camera it can be determined, how the segmenting process of the SAWs and the division of the image field of the camera into image field segments should be carried out. This division should preferably be carried out in an interactive mode, wherein well-known pointing and display means, such as a keyboard, a display screen and/or a mouse can be used, however, not limited thereto.

The present invention also provides an apparatus for processing the image data of the surface of a wafer recorded by at least one camera. The apparatus comprises a means for creating the above-described relative movement between the wafer and the at least one camera. An image field is formed for each camera. The M utility programs are provided by an evaluation electronics. As already described above, the apparatus can comprise at least one frame grabber. The division into groups and the indexing can be carried out by a corresponding DP system. Imaging can be carried out by a line or array camera, and a constant light source. The relative movement between the wafer and the at least one camera can preferably be continuous.

BRIEF DESCRIPTION OF THE DRAWINGS

The method and the apparatus according to the present invention will be described in the following with reference to the schematic drawings in more detail, in which:

FIG. 5 is a top view of a portion of the wafer, wherein the individual elements of the portion and a further example of a combined index are shown;

DETAILED DESCRIPTION

Figure 1:
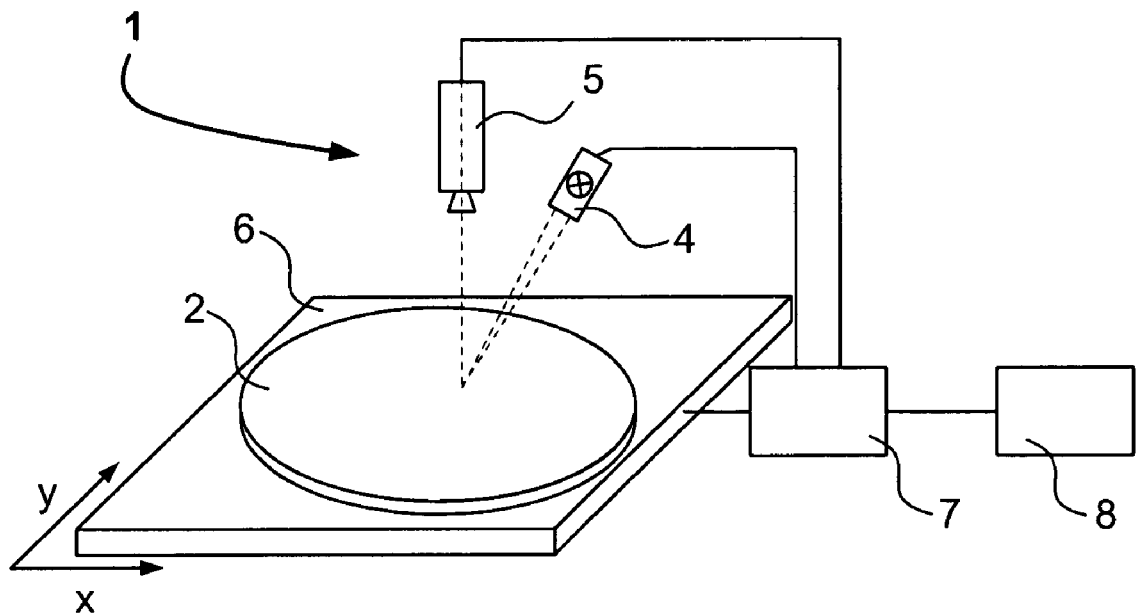
FIG. 1 schematically shows an apparatus for recording an image.

FIG. 1 schematically shows an apparatus 1 for processing image data of the surface of a wafer 2 recorded by a camera 5 according to the prior art. Wafer 2 is on a scanning stage 6. A plurality of images is taken of wafer 2 by means of camera 5. To create a relative movement between scanning stage 6 and camera 5, in the present exemplary embodiment, an X/Y scanning stage is used traversable in the X coordinate direction and/or the Y coordinate direction. Camera 5 is fixed with respect to scanning stage 6. Of course, scanning stage 6 can also be fixed, and camera 5 can be moved across wafer 2 for imaging. A combination of the movement of camera 5 in one direction and scanning stage 6 in the direction perpendicular thereto is also possible. Devices such as motors for moving the scanning stage and the camera can be provided.

Wafer 2 is illuminated by means of an illumination means or illuminator 4, which illuminates at least those areas on wafer 2 which essentially correspond to image field 15 (see FIGS. 3, 4, 5) of camera 5. Due to the concentrated illumination, which can additionally be pulsed with the aid of a flash lamp, imaging on-the-fly is possible, wherein scanning stage 6 or camera 5 is traversed without being stopped for the imaging process. In this way a great wafer throughput is possible. Of course, the relative movement between scanning stage 6 and camera 5 can also be stopped for each individual image, and wafer 2 can also be illuminated across its entire surface. Scanning stage 6, camera 5 and illuminating means 4 are controlled by a control unit 7. The images can be stored in a computer 8 and further processed therein, as the case may be.

Figure 2:
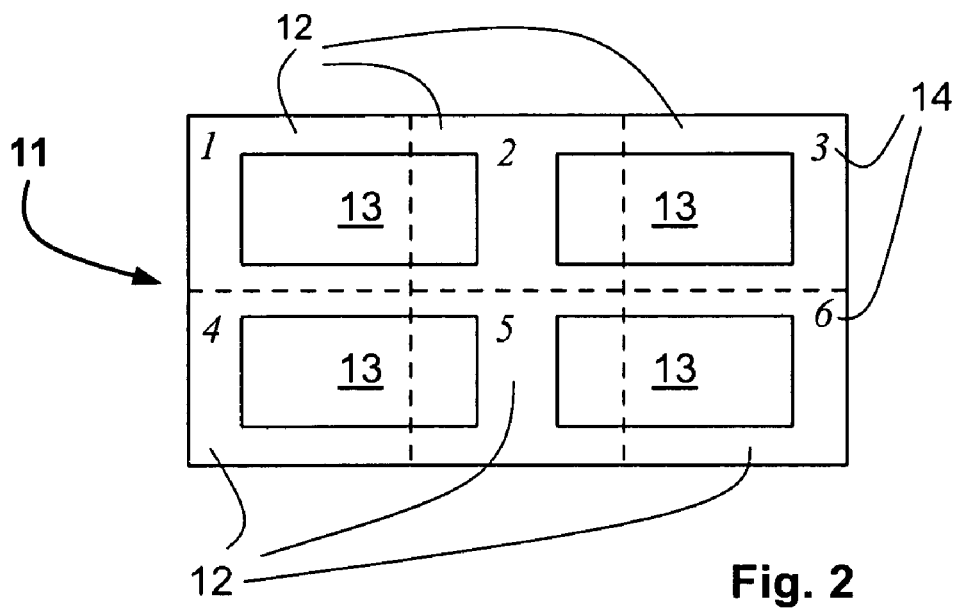
FIG. 2 schematically shows a logically segmented SAW with corresponding SAW segment index numbers.

FIG. 2 is a schematic view of a logically segmented SAW 11 subdivided into six SAW segments 12, indicated by the two vertical broken lines and one horizontal broken line. SAW 11 contains a plurality of dies 13, in FIG. 2, for example, four dies 13. Each of the six SAW segments 12 is indicated with a sequential SAW segment index 14. In the present case, this SAW segment index 14 extends from number 1 to number 6.

Figure 3:
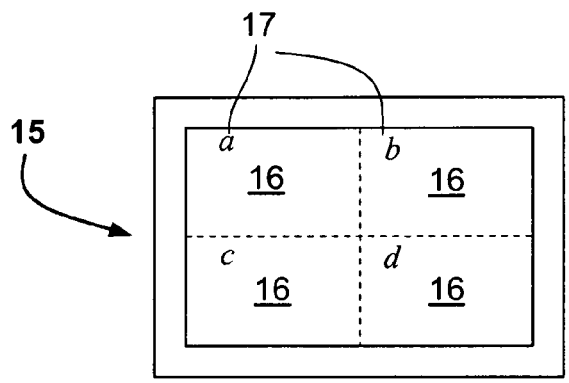
FIG. 3 schematically shows an image field of a camera with image field segment index letters of logical SAW segments capable of being imaged.

FIG. 3 schematically shows an image field 15 comprising four image field segments 16 indicated with the letters a to d as image field segment index 17.

Figure 4:
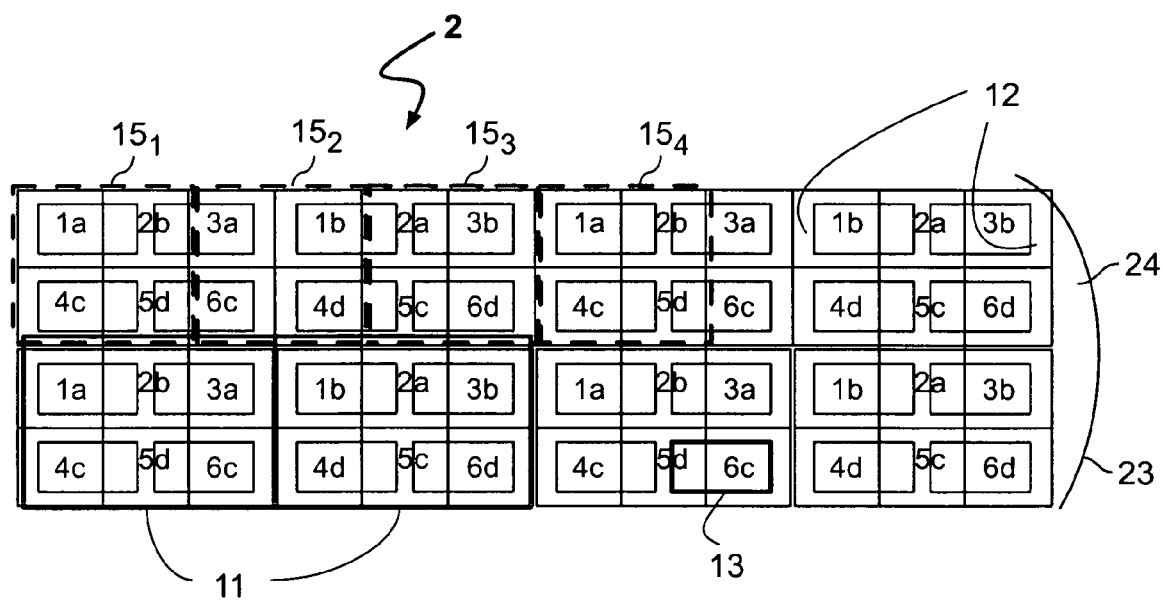
FIG. 4 is a top view of a portion of the wafer, wherein an example of a combined index is shown.

FIG. 4 shows a portion or section of a wafer 2 with a wafer edge 23, and an edge area 24, which is ignored when analyzing the respective portions of an image of edge area 24 to be inspected. The SAWs 11 arranged adjacent and below one another are each subdivided into six SAW segments 12 in the embodiment shown here, wherein two SAWs 11 are highlighted with bold lines at the bottom left of FIG. 4 in an exemplary manner. SAWs 11 cover the surface of wafer 2. In each SAW 11, the six SAW segments 12 receive the numbers 1 to 6 as an SAW segment index 14. Four dies 13 are arranged on each SAW 11.

When one of cameras 5 records images of the surface of wafer 2, it can only ever record that part of the surface of wafer 2 which corresponds to its image field 15. An image field 15 of camera 5 does not usually coincide with the surface area of an SAW 11 or an SAW segment 12. In FIG. 4 above, four image fields $15_1$, $15_2$, $15_3$ and $15_4$ are highlighted in an exemplary manner, which are each subdivided into four image field segments 16 (cf. FIG. 3). In each image field 15, the four image field segments 16 receive the letters a to d as an image field segment index 17.

By combining the two indices 14, 17, it is possible to determine which SAW segments 12 are covered by which image field segments 16. In the example according to FIG. 4, the first SAW segment 12, receives "1a" as a combined index. The first camera image with image field $15_1$ comprises image field segments 16 "1a", "2b", "4c", "5d". The second camera image with image field $15_2$ comprises image field segments 16 with a combined index "3a", "1b", "6c" and "4d". In a corresponding manner, the combined indices are continued with the third and fourth image fields $15_3$ and $15_4$. A repetition of the contents of image field 15 occurs at the first and fourth image fields $15_1$ and $15_4$. Thus the contents of the first and fourth image fields $15_1$ and $15_4$ can be compared with one another, because they are matched both in SAW segment index and in image field segment index 17.

Of course, both the individual image field segments 16 of first image field 15 can be compared to the corresponding image field segments 16 of fourth image field 15, and groups of image field segments 16 of the first to those of the fourth image field 15 can be compared, when there is an identical association. In other words: after three image fields 15, the contents are repetitive, i.e. N=3.

When the image field segments 16 are compared, it must be considered, however, that the distance of two SAW segments 12 with the same combined index does not become too large. If, for example, an SAW 11 was subdivided into six logical segments in the X direction, and if image field 15 of camera 5 only records five segments, the structures are repeated only every six images, when they are completely filled (according to the smallest common multiple of 5 and 6=30 SAW segments, repetition of the images). If, however, only four SAW segments 12 are filled in one image field 15, the structures are repeated every three images (according to the smallest common multiple of 4 and 6=12 SAW segment repetition of the images).

A displacement of the SAWs 11 with respect to each other (not shown in FIG. 4), as it is used to better exploit the wafer surface, can be treated likewise according to this approach. When image field 15 is advantageously filled, no separate groups are necessary for these displaced SAWs 11.

Edge areas 24 of wafers 2 are often ignored, as shown at reference numeral 24. At edge area 24 of a wafer 2, an SAW 11 is not fully projected, so that only part of an SAW 11 need be processed in the image processing. A corresponding adjustment is possible in the initialization step to take this condition into account. The substantial advantage is in the single training phase which is repeatedly taken into account during the process sequence when comparisons are carried out.

FIG. 5e is a top view of a portion of wafer 2, wherein the diverse elements of the portion are individually shown in FIGS. 5a-d for clarity. A further example of a combined index is shown here.

FIG. 5a shows a die 13. Each of the plurality of dies 13 is shown as a dot-dashed box in FIGS. 5a-e.

FIG. 5b shows an SAW 11 subdivided into nine SAW segments 12 each arranged in three lines and three columns. Each of the nine SAW segments 12 comprises exactly one die 13. Thus there are nine dies 13 arranged on SAW 11 overall. Each of these dies 13 is provided with an SAW segment index 14 of between 1 and 9. Each of the plurality of SAWs 11 is shown as a broken-line box in FIGS. 5b-e.

As already described with reference to FIG. 4, an image field 15 (camera field) of camera 5 is usually not coincident with the area of an SAW 11 or an SAW segment 12. FIG. 5c shows how image fields 15 cover SAWs 11: exactly four image fields 15 cover each SAW 11. Herein, each individual image field 15 covers 1.5 times the height and width of a die 13 in the X direction and the Y direction, respectively. Each of the plurality of image fields 15 is shown as a box with a solid bold line in FIGS. 5c-e.

According to FIG. 5d, an individual image field 15 is subdivided into nine image field segments 16, each having an image field segment index 17 between a and i. Each of the plurality of image field segments 16 is shown as a box with a thin solid line in FIGS. 5d-e.

FIG. 5e shows all previously described elements, wherein only image fields 15 and image field segments 16 of the topmost line and the left column are highlighted in an exemplary manner for clarity. Four SAWs 11 are shown, two for each line and column. As already described with reference to FIG. 4, by combining the two indices 14, 17 it can be determined which SAW segments 12 are covered by which image field segments 16. In the example according to FIG. 5e, the combination of indices 14, 17 is carried out in an analogous fashion to FIG. 4. In the example according to FIG. 5e, the contents are repeated after four image fields 15, image fields $15_1$ to $15_4$ are different, but image fields $15_1$ and $15_5$ are the same, i.e. N=4, since there are four groups with identical association.

Figure 6:
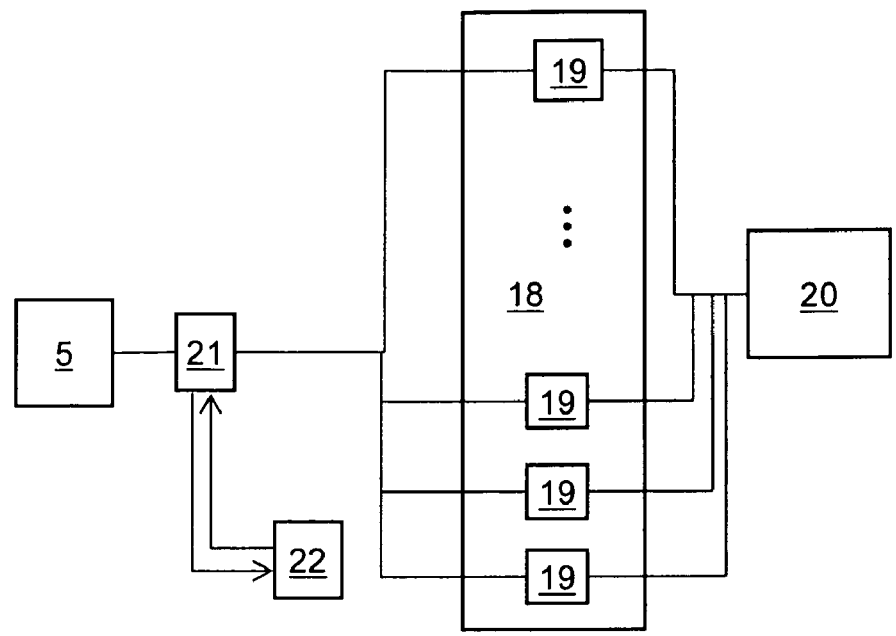
FIG. 6 schematically shows a portion of an embodiment of the apparatus, wherein a camera, a frame grabber and a control means are provided.

FIG. 6 is a schematic view of a portion of an embodiment of apparatus 1 with only one camera 5. A frame grabber 21 is coupled to camera 5. Frame grabber 21 is connected to a control means 22, which informs frame grabber 21, as noted above, which utility program 19 is assigned for the individual images of the present image group. The images recorded by camera 5 are then transmitted, as also described above, via frame grabber 21 to the appropriate utility program 19. Herein only images having the same image contents of image fields 15 out of the plurality of recorded images are transmitted, as described above, to each appropriate utility program 19. For better clarification of the functioning of apparatus 1, the subdivision of image fields 15 in FIG. 4 is referred to. The image contents of image fields $15_1$ and $15_4$ of FIG. 4 are the same because they both have the same combined indices "1a", "2b", "4c" and "5d". In the present example, the image contents are thus repeated after N=3 image fields 15. One and the same utility program 19 is therefore only provided with the image contents of every fourth image field 15 of an image group.

The individual results of utility programs 19 are forwarded to a central program 20 after receipt. An evaluation electronics 18 comprises utility programs 19. It goes without saying for a person skilled in the art that central program 20 can also be integrated in evaluation electronics 18. The number of utility programs 19 is not fixed but depends on the number N of images, after which the image contents of image fields 15 is repeated, as will be described in further detail below.

Figure 7:
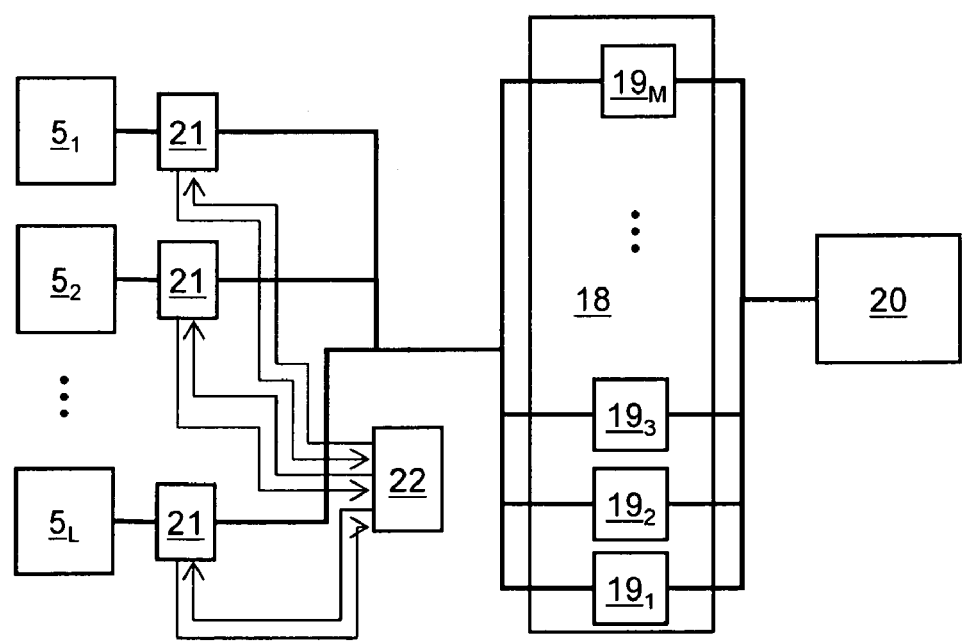
FIG. 7 schematically shows a portion of a further embodiment of the apparatus with a control means and a plurality of cameras each with a frame grabber.

FIG. 7 shows a schematic view of a section of a further embodiment of apparatus 1 with L>=2 cameras 5. One frame grabber 21 is associated with each camera 5. Each of the L frame grabbers 21 is connected with a control means or controller 22. Control means 22 determines each appropriate utility program 19 for each of the L frame grabbers and returns the answer to each frame grabber 21, as described above. Each of the L cameras 5 records images, immaterial in which order and with which line distances, although in practice usually a fixed imaging method is followed. The recorded images are forwarded from cameras 5 to each associated frame grabber 21 and sent on to control means 22. Control means 22 supplies the answer for each appropriate utility program 19 to each frame grabber 21. Each frame grabber 21 now supplies the recorded images according to the respective image contents and as commanded by control means 22 to the appropriate one of the M utility programs 19. The processes per camera 5 can be parallel and simultaneous since all above-described elements work independently of each other and therefore result in an increase in efficiency.

As already described with reference to FIG. 6, only images having the same image contents of image fields 15 from the plurality of recorded images are fed to each appropriate utility program 19 in an evaluation electronics 18, and the individual results of utility programs 19 are forwarded to a central program 20 after receipt. It goes without saying for a person skilled in the art that control means 22 can also be integrated into central program 20.

Figure 8:
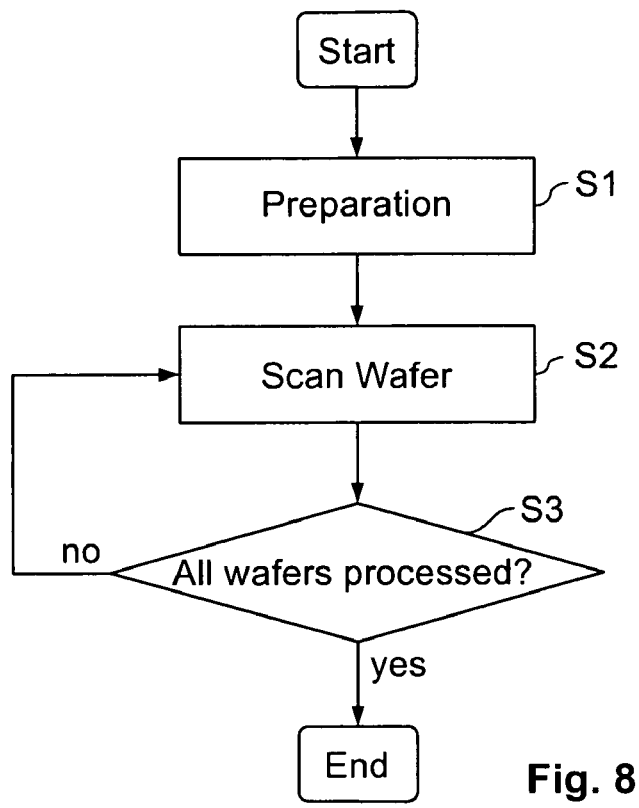
FIG. 8 is a flow chart of an embodiment of the method according to the present invention, wherein the sequence is shown in rough blocks.

FIG. 8 is a flow chart of an embodiment of the method according to the present invention with a camera 5, wherein the sequence of steps of the method is shown in rough blocks. The method can be subdivided into two partial steps S1 and S2, a preparatory phase S1 and the actual processing of the at least one wafer 2 in step S2. If more than one wafer 2 is processed, sub-step S2 is correspondingly repeated (query in step S3) until all wafers 2 have been processed.

Figure 9:
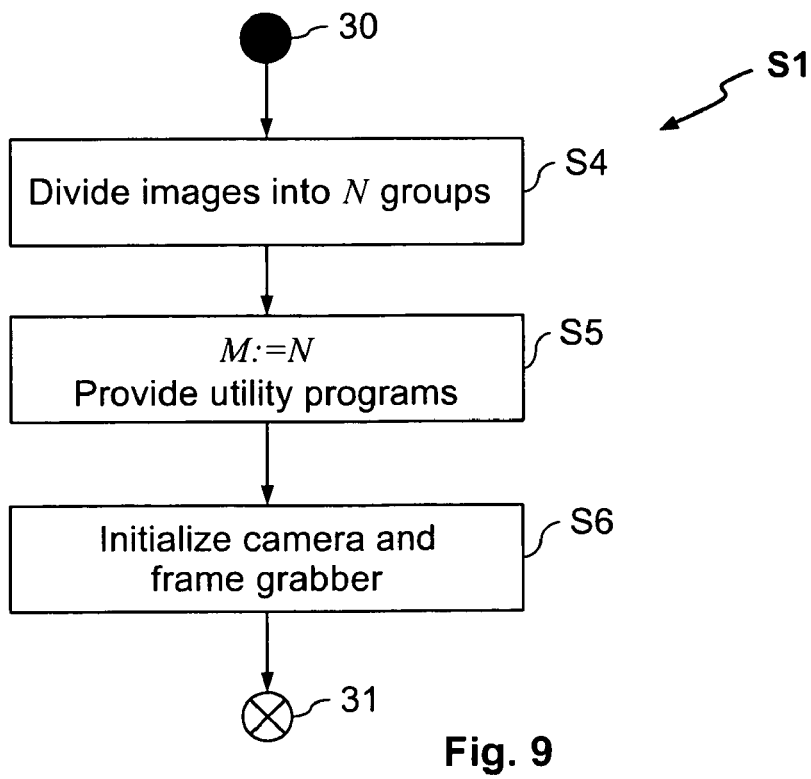
FIG. 9 is a flow chart of an embodiment of the sequence of the preparatory steps in the method according to the present invention.

FIG. 9 is a flow chart of an embodiment of the preparatory phase according to step S1 in FIG. 8 of the method according to the present invention which is carried out at entry point 30. Herein, step S1 is subdivided into sub-steps S4, S5, S6. At the beginning of the preparatory phase, in sub-step S4, the images are divided into N groups. The number N of groups and the assignment of the images to the groups is determined. In the following sub-step S5, M utility programs 19 are provided according to the number of groups N. In the last sub-step S6, camera 5 and frame grabber 21 are initialized. The next sequence of steps is entered into at continuation point 31.

Figure 10:
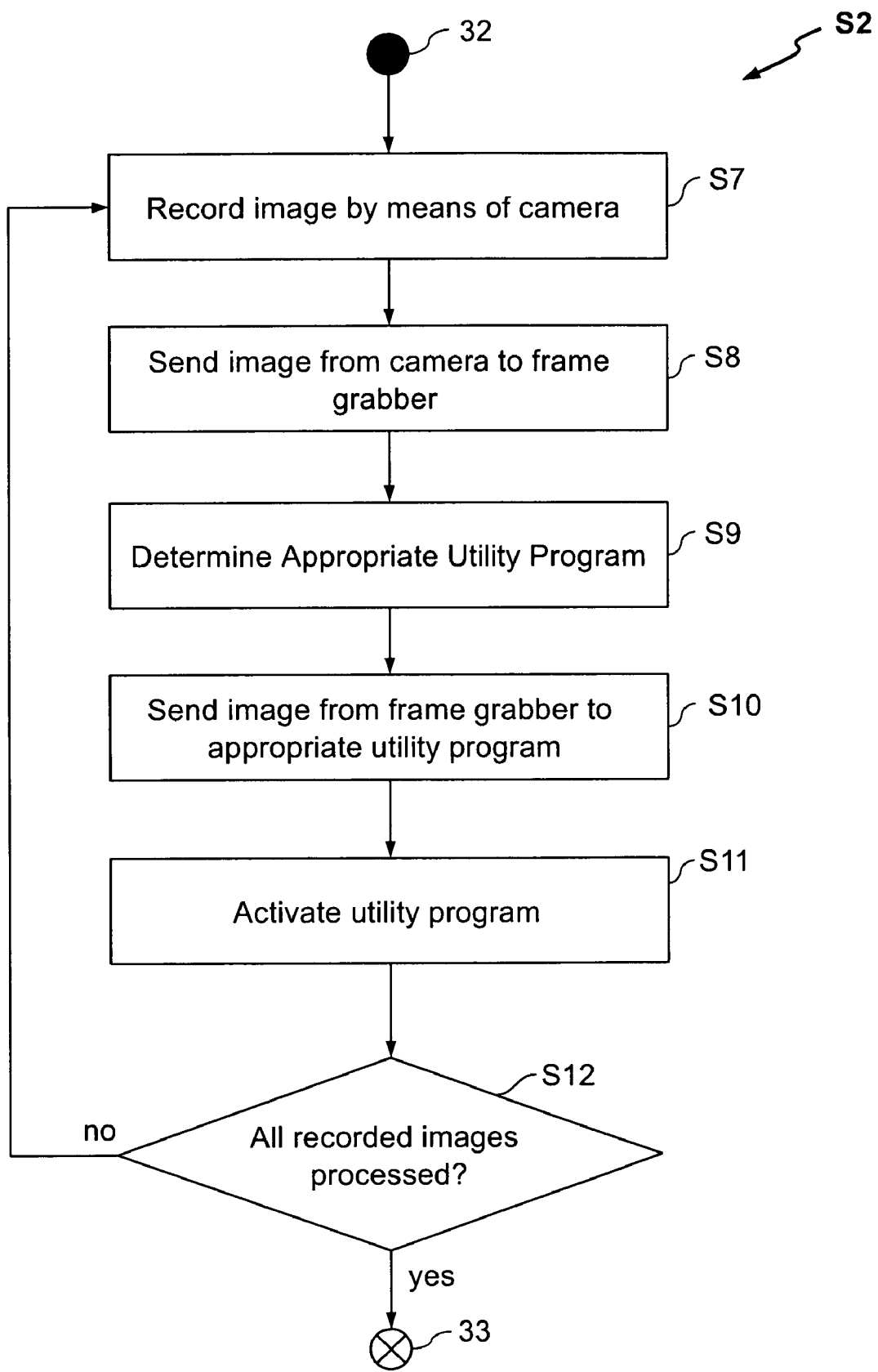
FIG. 10 is a flow chart of an embodiment of the sequence of the actual wafer scan in the method according to the present invention.

FIG. 10 is a flow chart of an embodiment for the sequence of the actual wafer scan according to Step S2 of FIG. 8 in the method according to the present invention, which is entered into at entry point 32. Here, step S2 is subdivided into sub-steps S7 to S12. First, an image is recorded by camera 5 (sub-step S7). Then the image is forwarded to frame grabber 21 by camera 5 (sub-step S8). Subsequently, it is determined which group the image belongs to, and therefore the appropriate utility program 19 is determined (sub-step S9). Then, the image data are transmitted from frame grabber 21 to the appropriate utility program 19 (sub-step S10). By this the appropriate utility program 19 is activated (sub-step S11) and the processing of the image is started in an asynchronous fashion. If not all images have been processed, the sequence is continued to sub-step S7 (query in sub-step S11). If all images have been processed, the process continues with step S3 of FIG. 8. The next sequence of steps is entered into at continuation point 33.

Figure 11:
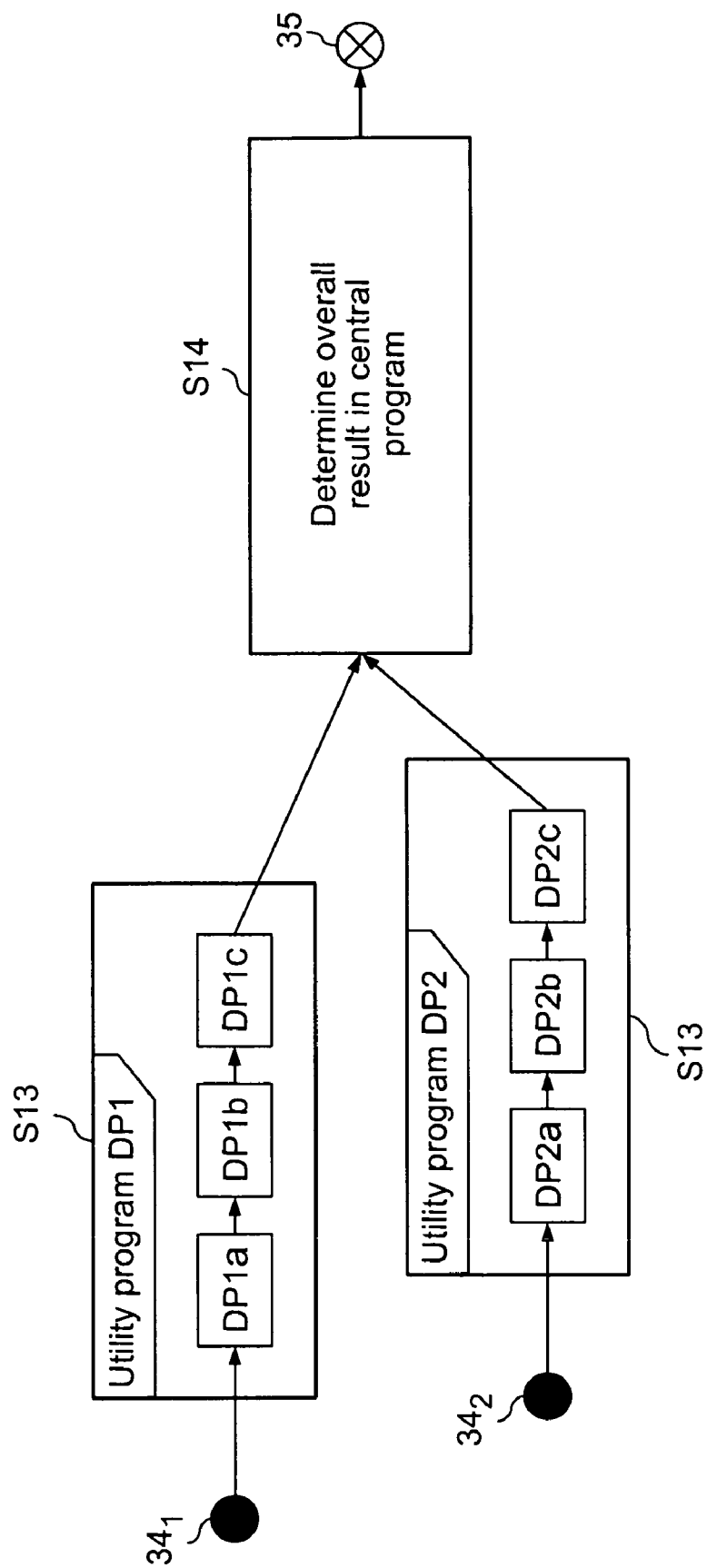
FIG. 11 is a flow chart of an embodiment of the sequence of processing the image information in the utility programs and the generation of the overall result in the method according to the present invention.

FIG. 11 is a flow chart of an embodiment with two utility programs 19, i.e. N M=2, for the image processing sequence running parallel to step S2 in the method according to the present invention. The two utility programs 19 DP1 and DP2 also function in parallel and independently from each other (steps S13) due to the independence of the data and are entered into from entry point $34_1$ or $34_2$. Within a utility program 19, various data processing steps DPa, DPb, DPc, DPd (not shown) etc. are carried out sequentially or in parallel. If new images are sent to a utility program 19 in step S10 as seen in FIG. 10, and this utility program 19 is activated in step 11, and if simultaneously the respective utility program 19 is still busy processing the preceding image in step S13, the new image to be processed is put into intermediate storage (latched) (not shown).

Step S2 is finished independently of the processing by the utility programs 19 in step S13 and the generation of the overall result in step S14. Thus the processing of the next wafer 2 can already be started in step S2, while the result of the preceding wafer 2 has not yet been completed. New utility programs 19 are generated, or old utility programs 19, having already finished processing of an image, are reused. These sub-steps are not shown in detail, however, in FIGS. 8 to 10, since they are well-known to the person skilled in the art. In step S13, the utility programs "know" how many images they have to process and indicate to central program 20 via step S14 when they have finished processing all the images.

Utility programs 19 DP1 and DP2 furnish a result to a central program 20 which determines the overall result for wafer 2 (step S14). The next sequence of steps is entered into at continuation point 35.

In embodiments with greater N=M, all M utility programs 19 DP1, DP2, . . . , DPM work independently of each other in a corresponding fashion.

Figure 12:
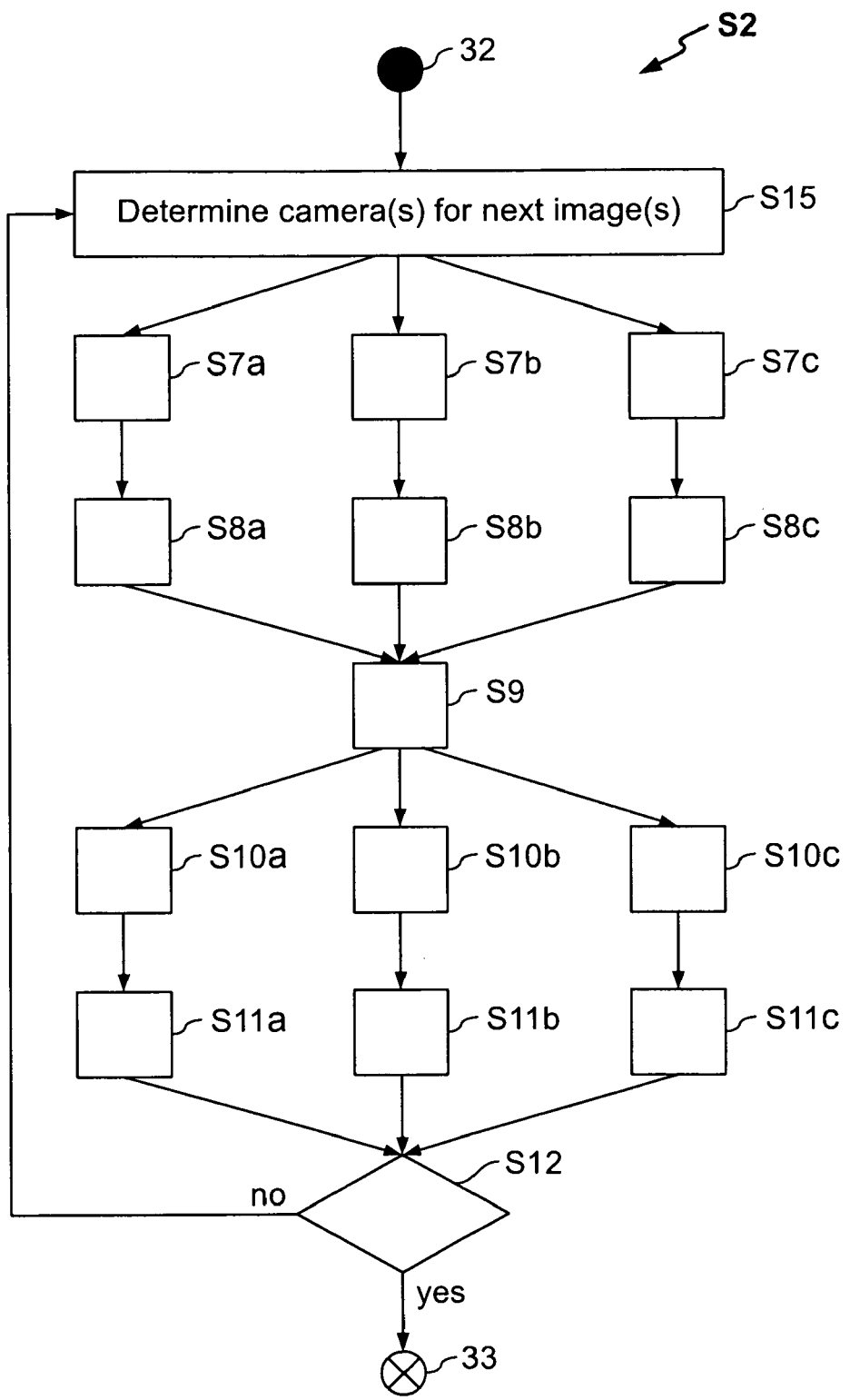
FIG. 12 is a flow chart of the sequence of a further embodiment of the method according to the present invention with a plurality of cameras for recording the images from the surface of the wafer.

FIG. 12 shows an embodiment with a plurality of cameras 5, here with three cameras 5 *a, b, c* (L=3). Only step S2 is shown, since steps S1 and S3 from FIG. 8, as well as the processing shown in FIG. 11, are only different in that a plurality of cameras 5 and frame grabbers 21 are used.

In an additional sub-step S15, in comparison to the embodiment according to FIG. 10, it must be determined first which camera 5 or which cameras 5 should record the next image field 15 (sub-steps S7*a*, S7*b*, S7*c*). It is conceivable both that a plurality of cameras 5 simultaneously record the same image field 15, and that cameras 5 record the images in succession, in an alternating fashion. Once it has been determined which camera(s) 5 is/are to be activated for the next image field 15, the process continues with sub-steps S7 and S8 according to FIG. 10, wherein the latter are carried out for all active cameras 5 in parallel (sub-steps S7*a*-S7*c* and S8*a*-S8*c*). Then, in sub-step S9, control means 22 decides which utility programs 19 are to be used. Sub-steps S10*a-c* and S11*a-c* (corresponding to sub-steps S10, S11 in FIG. 10) are then, again, carried out in parallel. At the end, in sub-step S12, it is determined by control means 22 whether further images are to be recorded. The processing of the images with utility programs 19 is then carried out in analogy to the parallel sequence shown in FIG. 11.

Finally, it should be noted in particular that the present invention has been described with reference to a preferred embodiment. It goes without saying for a person skilled in the art, however, that variations and modifications are possible without departing from the scope of protection of the appended claims.

What is claimed is:

1. A method for processing image data of the surface of a wafer recorded by at least one camera, comprising the steps of:
    defining an image field for each of at least one said camera in such a way that the recorded image content of said image field is repeated after N recorded images, wherein N is equal to or greater than two;
    determining M utility programs in an evaluation electronics, wherein M is equal to the number of recorded images after which the image content of the image fields is repeated, and adapting the number M of utility programs to the number of N images;
    feeding only images having a same image content of the image fields from the plurality of recorded images to each of the M utility programs to detect defects based on the image content of the image fields of the images from the surface of the wafer; and
    sequentially feeding the respective results of said M utility programs to a central program, the central program compiling a distribution of the defects present on the surface of the wafer from the individual results of said M utility programs;
    wherein a relative movement is carried out between the wafer and the at least one camera to record the image data of the surface of a wafer with the at least one camera.

2. The method according to claim 1, wherein each of said cameras is connected to one frame grabber respectively, having their outputs coupled to a controller, wherein said controller determines for each frame grabber which utility program is appropriate as a function of the image contents of the image fields of each camera and indicates the appropriate program to the respective frame grabber, and then the recorded images are transmitted from each frame grabber to the previously determined utility program as a function of the image contents of the image fields.

3. The method according to claim 1, wherein said image fields of said cameras are adapted to the structures on the wafer created with the aid of a stepper area window (SAW) in such a way that the image contents of said image field is repeated after a predefined number N of recorded images.

4. The method according to claim 3, wherein the size of the image field is defined in such a way that, in an initializing step, each SAW is subdivided into regular, equally sized logical SAW segments, wherein each SAW segment has an SAW segment index associated therewith, in that said image field of said camera is subdivided into SAW-segment-imaging image field segments in such a way that after a predetermined interval of recorded image fields a repetition of an identical association of imaged SAW segments occurs in image field segments, wherein said image field segments are smaller, larger or displaced with respect to the SAWs, so that the repetition interval is greater than one.

5. The method according to claim 4, wherein said logical SAW segments and said image field segments are indexed in each case, and said image fields have a combination of the SAW segment index and the image field segment index associated with them, on the basis of which a determination of the image field segments to be compared is carried out, wherein those image field segments are compared to each other which have an identical combination of the SAW segment index and the image field segment index.

6. The method according to claim 1, wherein a line camera and/or an array camera is used as said camera for making microscopic and/or macroscopic recordings of images.

7. The method according to claim 1, wherein the camera is a line camera and said wafer is illuminated by a constant light source.

8. The method according to claim 1, wherein a relative movement between said wafer and said camera is created which is continuous.

9. The method according to claim 1, wherein an image is recorded by a flash lamp triggered as a function of the relative position of said wafer to said camera and while the shutter is open.

10. The method according to claim 3, wherein the size of the SAWs is transmitted and the corresponding dies are marked, so that based on knowledge about the size of the image field of said camera it can be determined how the segmenting process of the SAWs and the subdivision of the image field of said camera into image field segments should be carried out.

11. The method according to claim 10, wherein this subdivision is interactively carried out, wherein a pointing and display device is used.

12. The method as recited in claim 11 wherein the pointing and display device include at least one of a keyboard, a display screen and a mouse.

13. An apparatus for processing image data of the surface of a wafer recorded by at least one camera, comprising:
    means for creating a relative movement between the wafer and the at least one camera;
    an image field is assigned to each camera, wherein said image field of each camera is adapted in such a way that the recorded image content of said image field is repeated after N recorded images, wherein N is equal to or greater than two;

an evaluation electronics with M utility programs, wherein M is equal to the number of recorded images after which the image content of the image fields is repeated, and in that the number M of utility programs is adapted to the number N of images, in that each of the M utility programs only receives images from the plurality of recorded images having the same image content of the image fields, in order to detect defects on the basis of the image content of the image fields of the images of the surface of the wafer; and a central program which sequentially receives the individual results of the M utility programs and compiles a distribution of the defects present on the surface of the wafer from the individual results of the M utility programs.

14. The apparatus according to claim 13, wherein each of said cameras is connected to one frame grabber, respectively, having their outputs coupled to a controller, wherein said controller determines for each frame grabber which utility program is appropriate as a function of the image contents of the image fields of each camera and indicates this to the respective frame grabber, and then the recorded images are transmitted from each frame grabber to the previously determined utility program as a function of the image contents of the image fields.

15. The apparatus according to claim 13, wherein said image fields of said cameras are adapted to the structures on the wafer created with the aid of a stepper area window (SAW) in such a way that the image content of said image field is repeated after a predefined number N of recorded images.

16. The apparatus according to claim 13, wherein a line camera and/or an array camera is used as said at least one camera for making microscopic and/or macroscopic recordings of images.

17. The apparatus according to claim 16, wherein a constant light source illuminates the surface of said wafer and in that a line camera records said images of said surface with the predefined image field.

18. The apparatus as recited in claim 13, wherein the means for creating a relative movement includes a scanning stage, at least one of the scanning stage and the camera being moveable.

19. An apparatus for processing image data of the surface of a wafer, comprising:

a camera for recording the image data;

a scanning stage, at least one of the scanning stage and the camera being movable for creating a relative movement between the wafer and the at least one camera;

an image field is assigned to each camera, wherein said image field of each camera is adapted in such a way that the recorded image content of said image field is repeated after N recorded images, wherein N is equal to or greater than two;

an evaluation electronics with M utility programs, wherein M is equal to the number of recorded images after which the image content of the image fields is repeated, and in that the number M of utility programs is adapted to the number N of images, in that each of the M utility programs only receives images from the plurality of recorded images having the same image content of the image fields, in order to detect defects on the basis of the image content of the image fields of the images of the surface of the wafer; and a central program which sequentially receives the individual results of the M utility programs and compiles a distribution of the defects present on the surface of the wafer from the individual results of the M utility programs.

* * * * *